(12) United States Patent
Donzier et al.

(10) Patent No.: US 9,952,192 B2
(45) Date of Patent: Apr. 24, 2018

(54) PROBE, SONDE AND METHOD FOR PRODUCING SIGNALS INDICATIVE OF LOCAL PHASE COMPOSITION OF A FLUID

(71) Applicant: Openfield SA, Versailles (FR)

(72) Inventors: Eric Donzier, Berchéres sur Vesgre (FR); Emmanuel Tavernier, Paris (FR); Linda Abbassi, Montigny le Bretonneux (FR)

(73) Assignee: OPENFIELD SA, Versailles (FR)

( * ) Notice: Subject to any disclaimer, the term of this patent is extended or adjusted under 35 U.S.C. 154(b) by 340 days.

(21) Appl. No.: 14/582,740

(22) Filed: Dec. 24, 2014

(65) Prior Publication Data

US 2015/0275661 A1    Oct. 1, 2015

(30) Foreign Application Priority Data

Mar. 28, 2014  (EP) ..................................... 14162506

(51) Int. Cl.
*G01N 33/28* (2006.01)
*G01N 21/17* (2006.01)
*G01N 27/02* (2006.01)
*E21B 47/10* (2012.01)

(52) U.S. Cl.
CPC ........... *G01N 33/28* (2013.01); *E21B 47/102* (2013.01); *G01N 21/17* (2013.01); *G01N 27/02* (2013.01); *G01N 33/2823* (2013.01)

(58) Field of Classification Search
CPC ............................. G01N 21/17; G01N 27/02
See application file for complete search history.

(56) References Cited

U.S. PATENT DOCUMENTS

| | | | | |
|---|---|---|---|---|
| 3,792,347 A | | 2/1974 | Hawley | |
| 5,661,237 A | * | 8/1997 | Dussan | E21B 47/102 324/324 |
| 7,474,971 B2 | * | 1/2009 | Hu | G01N 27/026 702/50 |
| 7,503,227 B2 | * | 3/2009 | Davis | G01F 1/66 73/861.42 |
| 8,299,796 B2 | * | 10/2012 | San Martin | G01V 3/24 324/303 |
| 2006/0139037 A1 | * | 6/2006 | Hughes | G01N 33/246 324/696 |

* cited by examiner

*Primary Examiner* — Harshad R Patel
*Assistant Examiner* — Jamel Williams
(74) *Attorney, Agent, or Firm* — The Jansson Firm; Pehr B. Jansson

(57) ABSTRACT

Probe for producing signals indicative of a local phase composition of a fluid flowing in a well, comprising a body of electrically insulating material having a tip adapted for contact with the fluid, at least two electrodes of conductive material located in the body on opposite sides relatively to a central axis of the body and insulated from each other, the electrodes having ends exposed to the fluid located on either side of the tip.

35 Claims, 11 Drawing Sheets

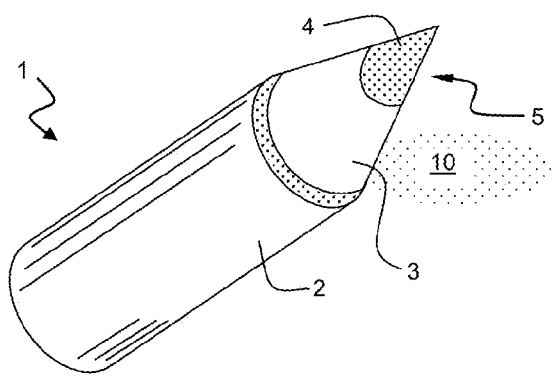
FIG. 1a – Prior Art
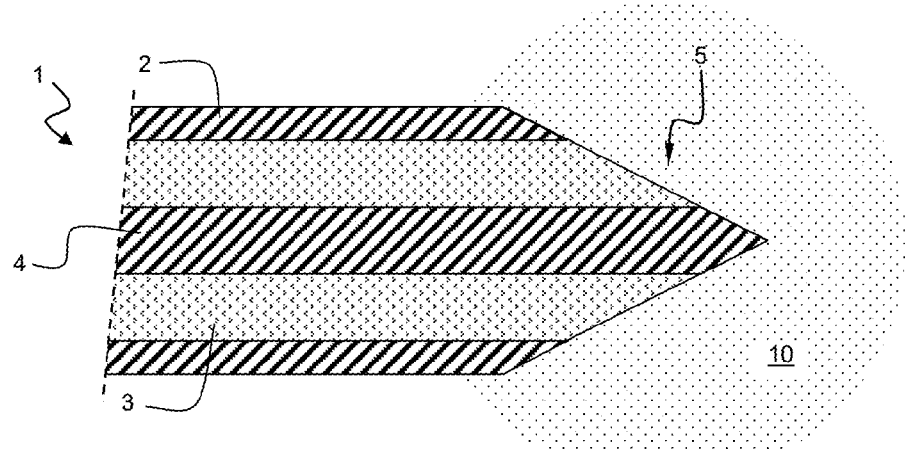
FIG. 1b – Prior Art
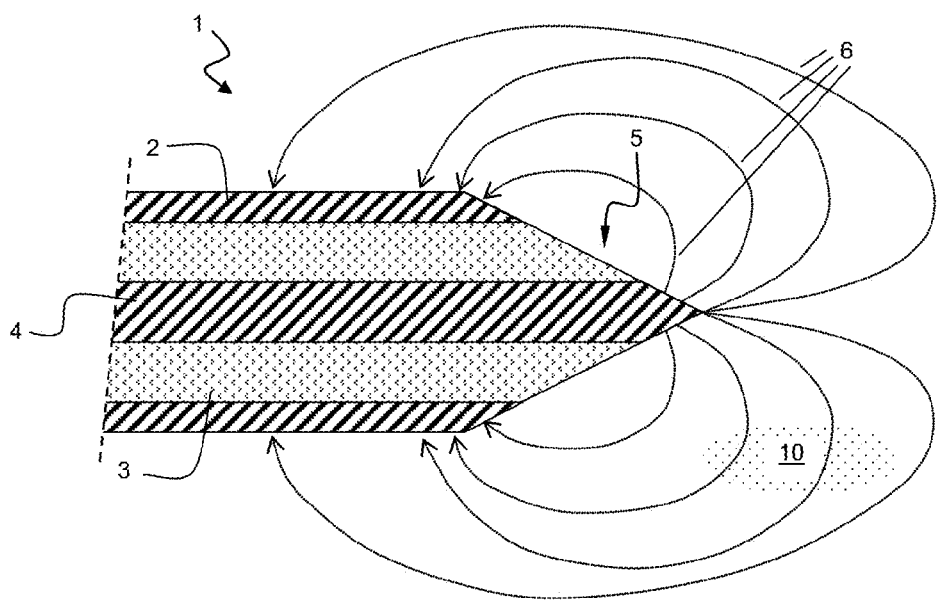
FIG. 1c – Prior Art

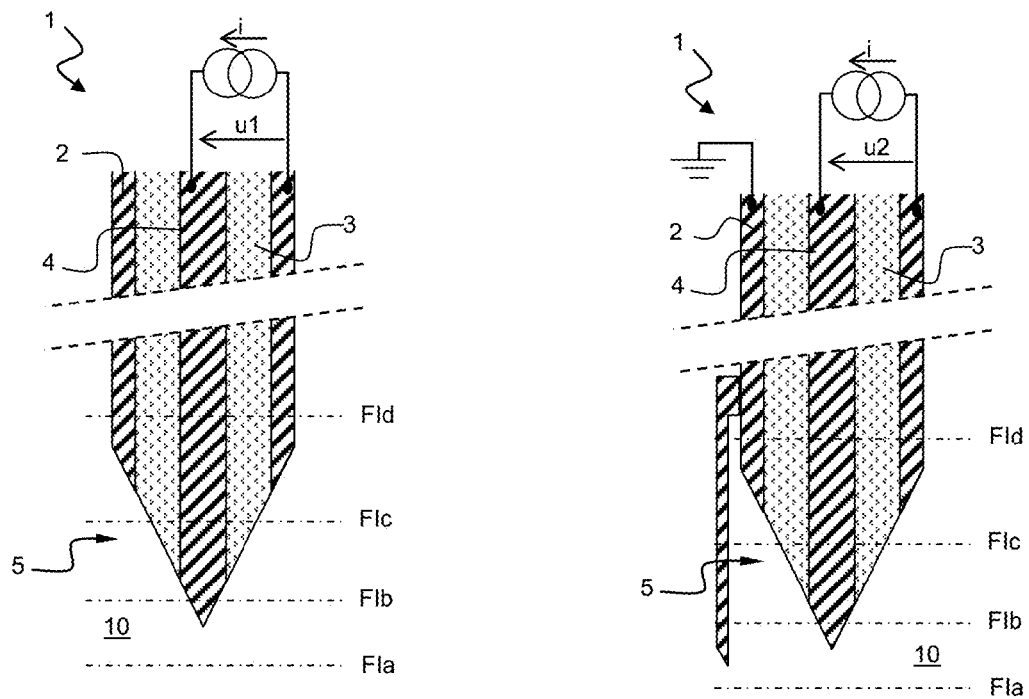
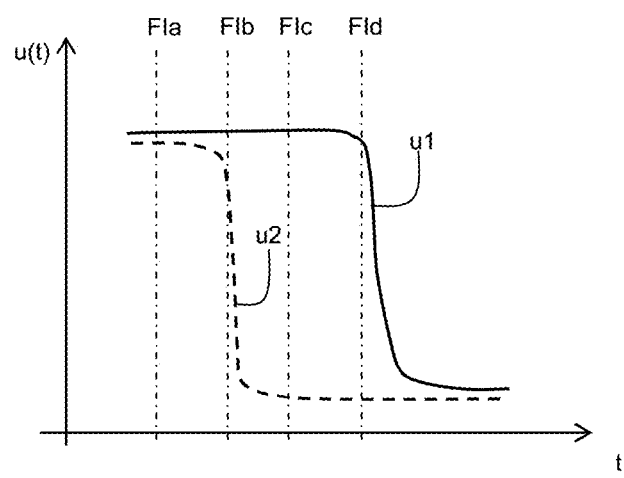
FIG. 1d – Prior Art

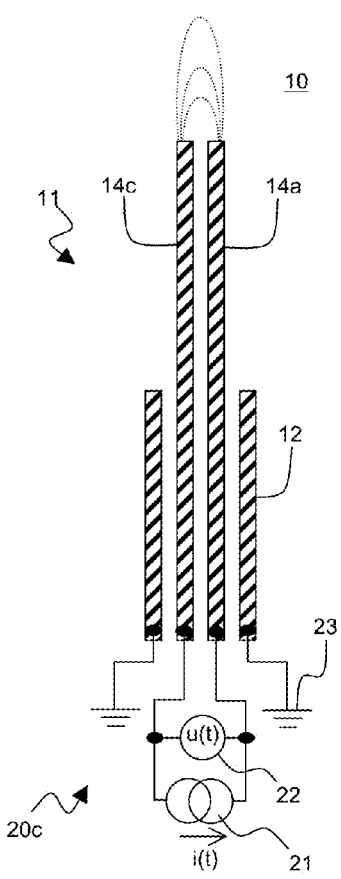
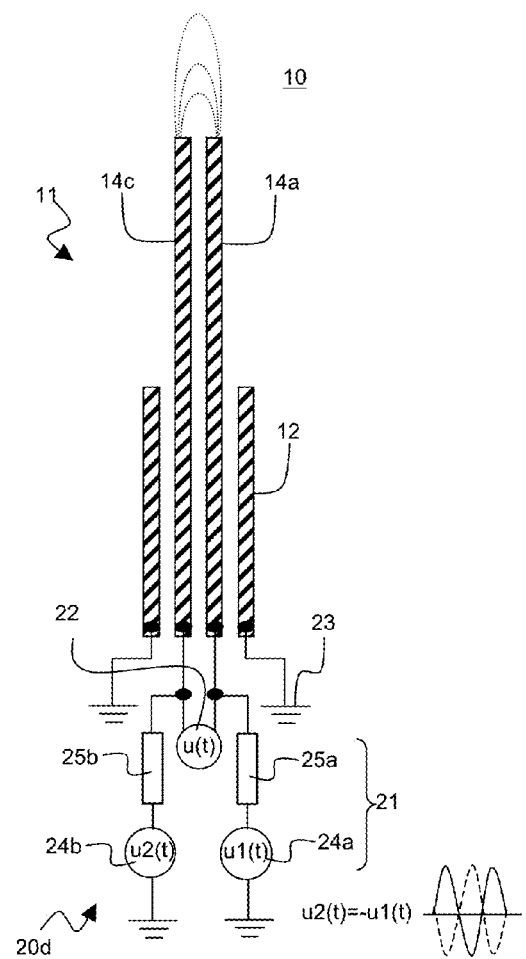
FIG. 3c  FIG. 3d

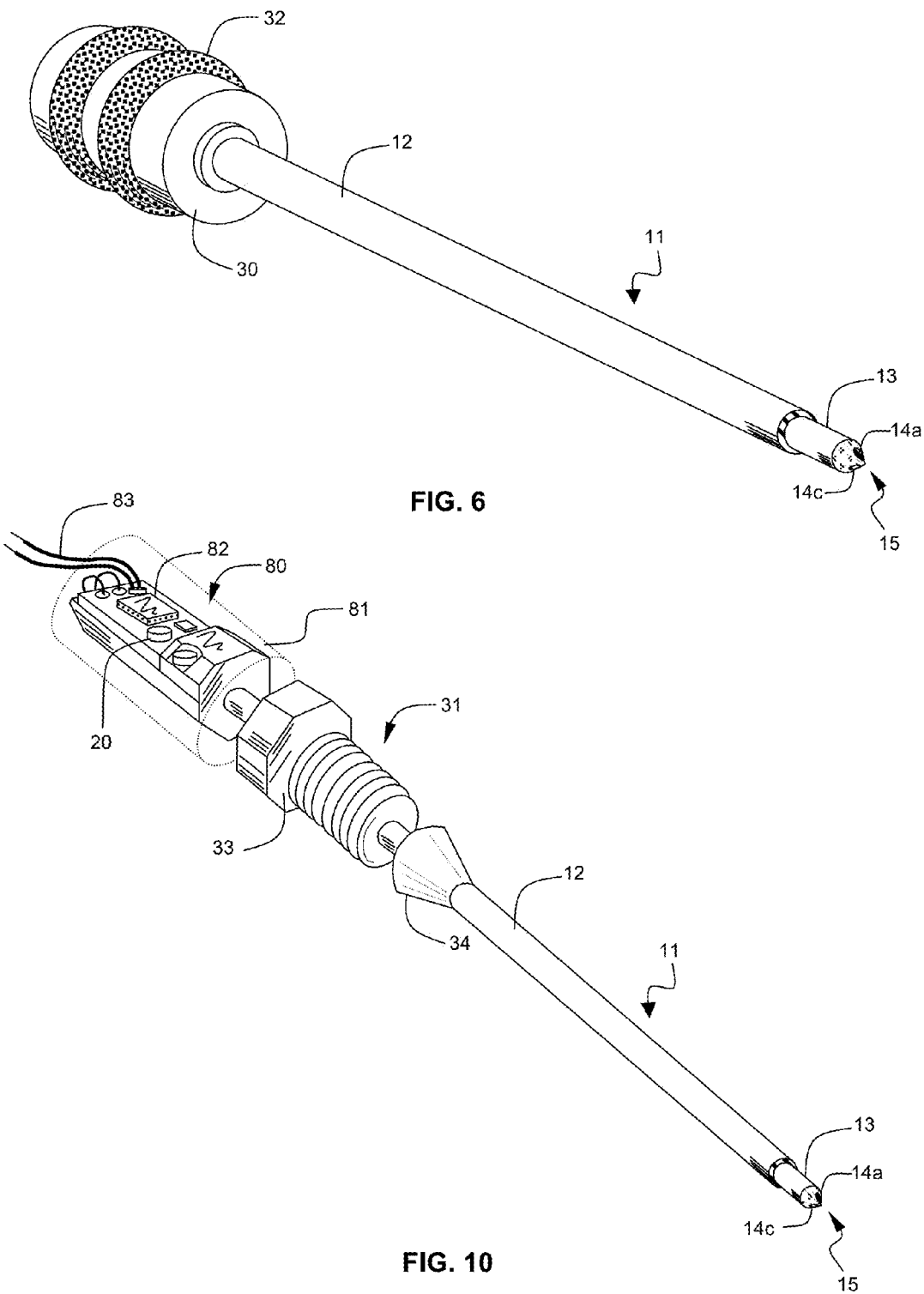

PROBE, SONDE AND METHOD FOR PRODUCING SIGNALS INDICATIVE OF LOCAL PHASE COMPOSITION OF A FLUID

TECHNICAL FIELD

The invention relates to a probe, a sonde and a method for producing signals indicative of a local phase composition of a fluid flowing in a well. The invention relates to the identification of phases and electrical properties characterization in a fluid flowing in a well by local measurements. The invention is particularly applicable to the identification of phases in the multiphase fluid containing water flowing in a hydrocarbon well by local measurements but it is also applicable in the context of injection wells in which the fluid flowing in the well includes injected fresh water and brine originated in the subsurface.

BACKGROUND

Multiphasic flows in hydrocarbon wells are very difficult to evaluate and measure as they can encounter complex flow regimes such as bubble, slug, mist or segregated flow depending on fluid properties, holdups, rates. Since hydrocarbon wells are generally deviated, sometimes highly deviated and even horizontal, the proportions of the phases (oil, gas, water) which make up the fluid flowing in the well are not homogeneous across a given section of the well and a mapping across the section is desirable.

In order to map the well section, local sensors are required for fluid identification, i.e. the evaluation of phase concentrations at each position of the well section.

The prior art discloses resistivity sensors for determining local phase concentrations in the fluid flowing in a hydrocarbon well.

The document U.S. Pat. No. 3,792,347 discloses the use of a plurality of needle-shaped sensing pointed electrodes. This document describes a tool for measuring the percent of oil in an oil/water mixture in an oil well. A plurality of electrodes is arranged in a substantially coextensive array in the flow path of the produced mixture at varying levels. Electrical arrangements are provided whereby a statistical analysis of the number of electrodes immersed in oil at a given moment may be integrated on a go-no go basis, the electrodes being either insulated when in oil or conducting to ground when in water. The number of electrodes so insulated by oil droplets being converted into an analogous electrical signal. Errors due to variations in the resistance and galvanic offset voltage in the water are compensated for.

The document U.S. Pat. No. 5,661,237 discloses a measurement sonde comprising a plurality of local resistivity probes. This document describes a method for producing, in a hydrocarbon well, a signal indicative of a local flow parameter of a multiphase fluid, includes the steps of placing at least one local sensor in the fluid and producing a signal whose level is characteristic of the phase in which the sensor is immersed, the signal being generated at a spike whose radius of curvature is less than 100 microns. The method is applicable to determining hold-ups of different phases of the fluid.

Electrical probes as disclosed in the document U.S. Pat. No. 5,661,237 have a coaxial structure. Such a probe according to the state of the art is depicted in FIGS. 1a, 1b, 1C and 1d. The probe 1 is composed of an external metal tube 2 and a central metal electrode 4 separated by an insulator 3. The tip 5 of the probe 1 is shaped into a cone in order to make a sharp end facilitating fluid 10 interface piercing. The measurement is made by measuring the impedance between the external electrode 2 (ground electrode) and the central electrode 4, which is related to fluid 10 resistivity, permittivity as well as probe geometry. FIG. 1a is an external view of such an electrical probe. The measurements enable detecting water in a multiphase fluid 10 flowing in hydrocarbon wells. FIG. 1b is a cross-section view of the tip 5 construction for such an electrical probe. FIG. 1c is a cross-section view showing current lines 6 extending in a large volume from the probe tip inducing large sensitivity to bubble/droplet sizes and continuous medium properties. FIG. 1d shows a probe response u(t) to a moving fluid interface for such an electrical probe (full line u1) and for an alternative electrical probe having an extended ground needle (dotted line u2). The moving fluid interface corresponds to the electrode penetrating an oil droplet in water. The probe response u(t) at various fluid interface Fla (before penetration), Flb (penetration at the end of the tip), Flc (half penetration of the tip) and Fld (full penetration of the tip).

The drawbacks of such a probe structure are the following:

The sensitivity extends far away from the probe tip leading to unstable measurements in multiphasic conditions. In particular the change of continuous medium from water to oil or gas has a large influence on measurements.

The measurement depends on electrode resistivity and contact resistance between metal and fluid where it is immersed. In high salinity brines the contribution of fluid resistivity to signal can become small leading to poor accuracy on measurements.

External electrical fields can generate parasitic currents in the external tube of the probe. In particular ground currents generated in the measurement sonde are difficult to isolate from the external tube of the probes and create noise in measurements.

Due to the above described limitations, it is not possible to accurately measure electrical properties of fluids. In practice such probes are used to discriminate water from oil and gas giving a digital-like signal. In particular it is not possible is to interpret water salinity.

Chemical and electromechanical effects can lead to the growth of an insulating layer at the metal surface degrading the mechanical integrity of the probes and altering measurements.

The time response is slow as transition requires a complete probe immersion in water up to the external tube metal contact in order to define a return path for the current.

The metal tip of the probe is facing the flow with maximum fluid velocity on its sharp end. In high flow conditions the sensitive element of the sensor is therefore submitted to erosion by solid particles such as sand grains embarked with flow leading to probe degradation in the field and alteration of signal over time.

Oil or water droplets can stick at the end of the probe, in particular at the insulator-metal interface.

SUMMARY OF THE DISCLOSURE

It is an object of the invention to propose a probe and/or a sonde and/or a method for producing signals indicative of local phase composition of a fluid flowing in a conduit that overcome one or more of the limitations of the existing methods and/or devices.

According to one aspect, there is provided a probe for producing signals indicative of a local phase composition of a fluid flowing in a well, comprising a body of electrically insulating material having a tip adapted for contact with the fluid, at least two electrodes of conductive material located in said body on opposite sides relatively to a central axis of the body and insulated from each other, said electrodes having ends exposed to the fluid located on either side of said tip.

The probe may comprise two electrodes, being simultaneously excitation and detection electrodes, said electrodes being adapted for connection to a measurement circuit comprising an excitation module in parallel with a measuring module, a signal in the electrodes measured by the measuring module being related to an electrical parameter indicative of the local phase composition of the fluid contacting the tip.

The probe may comprise a first pair of electrodes, being excitation electrodes, located in a first plane intersecting the central axis of the body, and a second pair of electrodes, being detection electrodes, located in a second plane intersecting the central axis of the body and at angle with the first plane, said first pair of electrodes being adapted for connection to an excitation module, said second pair of electrodes being adapted for connection to a measuring module.

The excitation module may comprise a first alternative voltage generator connected to a first electrode through a first shunt resistor, and a second alternative voltage generator connected to a second electrode through a second shunt resistor, said first and second alternative voltage generators generating excitation signals in phase opposition.

The probe may comprise a metal tube surrounding said body and acting as shield.

Each electrode may have a sheath of insulating material.

The tip of the body may be conical such as to define a tip conical surface, the electrodes ends exposed to the fluid emerging from the body in the tip conical surface, laterally from a tip end point.

The tip of the body may comprise two planar surfaces having different angles relatively to the central axis of the body, the electrodes ends exposed to the fluid emerging from the body in the planar surfaces, laterally from a tip end line.

The probe may comprise an optical element located in the central portion of the body, an end portion of said optical element forming the end of the probe tip.

The probe may comprise an electronic board connected to the body and integrating the measurement circuit and a processing module so as to deliver digital measurements on an output cable.

According to a further aspect, there is provided a measurement sonde adapted for displacement along and within a well, comprising a plurality of probes in accordance with the invention located at angularly distributed locations with respect to the central axis of the measurement sonde.

The well is a hydrocarbon well, and the measurement sonde carries centralizers, the plurality of probes being secured to the centralizers.

According to still a further aspect, there is provided a method for producing signals indicative of a local phase composition of a fluid flowing in a well, comprising the steps of:
  inserting a probe in the well, said probe comprising a body of electrically insulating material having a tip adapted for contact with the fluid, at least two electrodes of conductive material located in said body on opposite sides relatively to a central axis of the body and insulated from each other, said electrodes having ends exposed to the fluid located on either side of said tip,
  applying an excitation signal on two electrodes, said electrodes being excitation electrodes,
  measuring a detection signal related to an electrical parameter indicative of the local phase composition of the fluid contacting the tip on two electrodes, said electrodes being detection electrodes.

According to still a further aspect, there is provided an application of the method according to the invention for producing signals indicative of the local phase composition of a multiphase fluid flowing in a hydrocarbon well.

With the invention, it is possible to accurately measure electrical properties of fluids, namely discriminating water from oil and gas, interpreting water salinity, improve spatial resolution, reducing measuring signal disturbance, etc. . . .

Due to its design, the probe of the invention has a greater mechanical integrity and resistance to chemical, electromechanical, and erosion effects of the fluid to be measured than the probes of the prior art. This results in a greater accuracy and longer life duration.

Other advantages will become apparent from the hereinafter description of the invention.

BRIEF DESCRIPTION OF THE DRAWINGS

The present invention is illustrated by way of examples and not limited to the accompanying drawings, in which like references indicate similar elements:

FIGS. 1a, 1b, 1c and 1d show prior art electrical probes.

FIGS. 3a, 3b, 3c and 3d show various embodiments of measurement circuit (as equivalent electrical circuit) adapted to be coupled to the probe of FIGS. 2a and 2b.

FIG. 6 is a perspective view schematically showing a second embodiment of a probe having a high pressure feedthrough for integration in a well logging tool according to the invention;

FIG. 10 is a perspective view schematically illustrating a smart probe for integration in a measurement sonde of a production logging tool.

DETAILED DESCRIPTION

The invention will be understood from the following description, in which reference is made to the accompanying drawings.

Figure 2A:
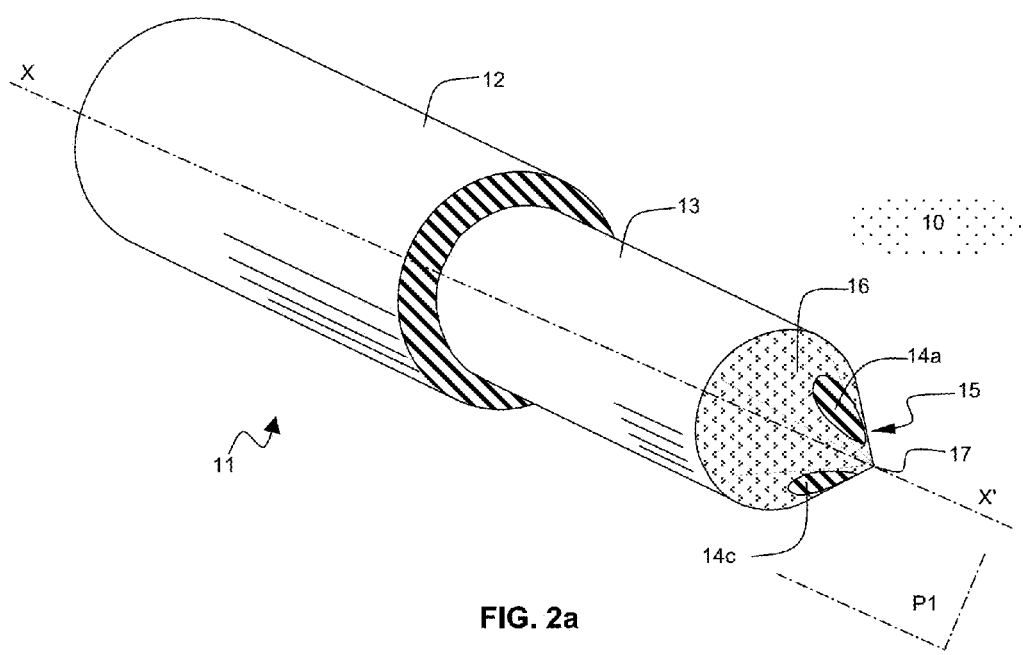
FIGS. 2a, 2b and 2c are perspective and cross section views showing a first and a second embodiment of a probe according to the invention, respectively.
Figure 2B:
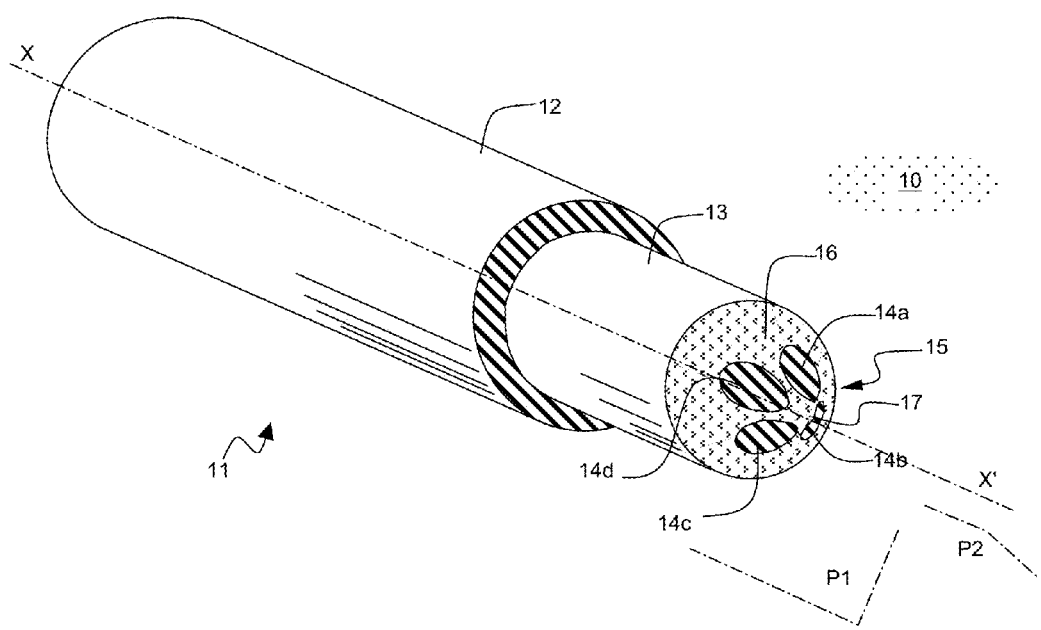
Figure 2C:
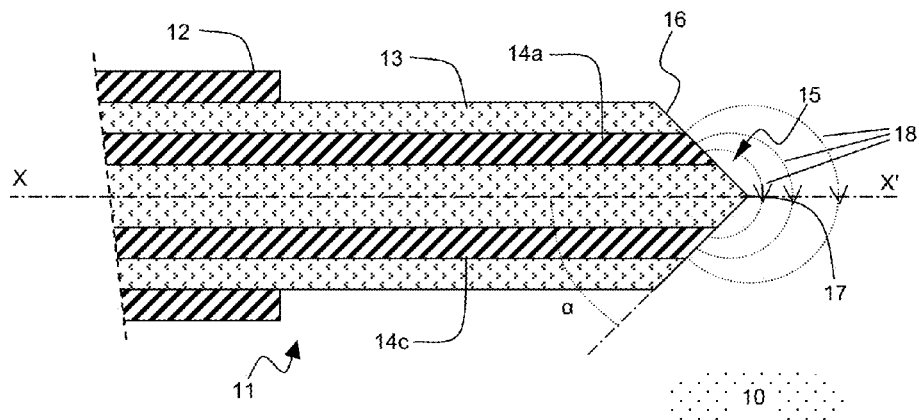

According to the embodiments of FIGS. 2a, 2b and 2c, a probe 11 comprises two (FIG. 2a) or four (FIG. 2b) wire electrodes 14a, 14b, 14c, 14d of conductive material located in an elongated body 13 of electrically insulating material, for example an insulating tube 13. Said electrodes 14a, 14b, 14c, 14d are located in the elongated body 13 on opposite sides (by pair of electrodes) relatively to a central axis XX' of the elongated body 13 such as to be insulated from each other.

The elongated body 13 of the probe 11 has a tip 15 having a needle shape, for example a conical shape. The end 17 of the tip 15 has the function of contacting the fluid, more precisely piercing the fluid 10. In the particular context of oilfield industry, this feature is helpful in order for the tip 15 to penetrate into oil or gas bubble flowing in water.

The probe 11 includes an external metal tube 12 surrounding the body 13 on at least a part of its total length. The metal tube 13 is used to mechanically protect the sensitive elements and electrically shields the signals leading to more robust and stable measurements. High strength high chemical resistance metal such as Inconel can suitably be used without issues related to low conductivity.

The ends of the electrodes 14a, 14b, 14c, 14d that emerge from the body 13 at the tip 15 define electrodes contacting surfaces. The electrodes contacting surfaces are positioned on tip surface 16 where fluid 10 is swept, i.e. the slope of the tip 15 of the insulating tube 13. Further, the electrodes contacting surfaces are positioned away from erosion zones, i.e. the end point 17 of the tip 15. Thus, the electrodes 14a, 14b, 14c, 14d ends exposed to the fluid 10 emerge from the body 13 in the tip surface 16, laterally from the tip end point 17. This ensures a fast response time and an improved resistance to erosion, respectively.

According to the two wire electrodes embodiment depicted in FIG. 2a, the two wire electrodes 14a, 14c are positioned in a first plane P1 intersecting the central axis XX' of the body. These two electrodes are simultaneously excitation and detection electrodes.

According to the four wire electrodes embodiment depicted in FIG. 2b, a first pair of wire electrodes 14a, 14c are positioned in a first plane P1 intersecting the central axis XX' of the body, a second pair of wire electrodes 14b, 14d are positioned in a second plane P2 also intersecting the central axis XX' of the body and at angle with the first plane P1. In the depicted and non limitative example, the first plane P1 and the second plane P2 are perpendicular to each other.

The probe is manufactured using a multi-channel ceramic tube (forming the elongated body in the shape of the insulating tube 13) into which metal wires (forming the electrodes 14a, 14b, 14c, 14d), made of a corrosion resistant metal such as Inconel, are inserted. The ceramic tube is mounted inside a metal tube 12 also made of high resistance metal such as Inconel. The metal wires sections inside the metal tube are covered with an insulating material such as PolyTetraFluoroEtylen. Probe assembly is made by gluing or brazing. The ceramic tube is then grinded in a needle shape and polished. A sealing piece 30 (best seen on FIG. 6) is mounted at the base of said tubes ensuring a pressure tight liaison with the measurement sonde 50 (best seen on FIG. 7a) carrying the probes and allowing wires to be connected to the electronics board 80 (best seen on FIG. 10). The sealing piece 30 may be either welded to the tube 12, or crimped using conical ferules 31 such as those commercialized by the companies Swagelok or Parker (best seen on FIG. 10). The metal wires may be covered with a thin film of gold or copper at their base in order to facilitate soldering to the electronics board. The deposition can be made using electrolytic methods. The sealing piece 30 may further be fitted with O-ring 32 (best seen on FIG. 6) for waterproof connection with the measurement sonde 50.

FIG. 2c is a cross-section view showing the probe 11 with current lines 18 localized at the probe tip 15. Such a probe allows accurate measurement of water resistivity even in multiphasic flow conditions. Further, it operates with a faster response time for better water holdup interpretation compared to probe of the prior art.

FIG. 10 shows a smart probe 11 for integration in production logging tools. The probe includes a conical ferule based high pressure metal-metal seal connection 31 (a screw 33 associated with a cone seal element 34 coupled to the external metal tube 12) and an electronics board 80. The electronic board 80 may be further protected by a protective housing 81. The electronic board 80 integrates a measurement circuit 20 and a processing module 82 that delivers digital signal on output cables 83. Such a probe 11 delivers fully calibrated conductivity measurement at a high data rate. The processing module 82 may be a microcontroller that computes in real time bubble counts, bubble size distribution, holdups and is user programmable for adjusting gains, excitation frequency and amplitude, etc. . . . All these computed data are available for further processing as digital signals on the output cables 83. The measurement circuit 20 will be described in details hereinafter.

Typical dimension of the probe tube is 1/16" (43 mm) outer diameter and 10 inches (254 mm) long. Typical angle $\alpha$ of the probe tip is 30 to 90°. Typical diameter of the probe is about 1 mm and typical diameter of electrodes is 100 to 300 μm.

Figure 3A:
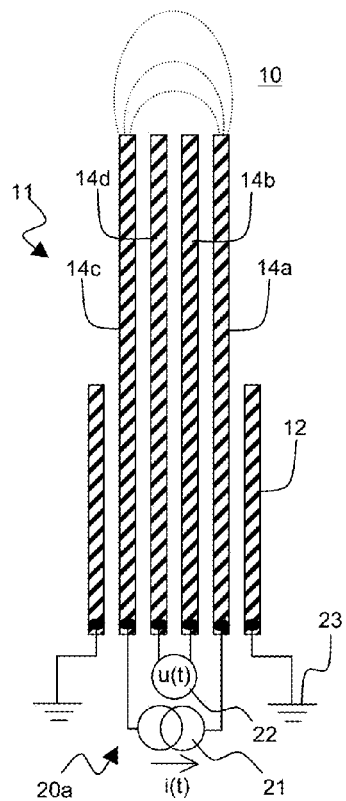

According to a first embodiment depicted on FIG. 3a, the measurement circuit 20a, adapted for a probe comprising four electrodes 14a, 14b, 14c, 14d, comprises an alternative current generator 21. The alternative current generator 21 forming an excitation module operates at frequencies ranging from a few kilohertz to a few Mega Hertz, and drives a sinusoidal current i(t) ranging from a few μA to a few mA. The alternative current generator 21 is connected to the excitation electrodes 14a, 14d. A voltage meter 22 forming a measuring module is connected to the detection electrodes 14b, 14d and measures the resulting voltage u(t). In the depicted example, the external tube 12 is connected to the ground 23. The measuring module may comprise amplification means, for example an operational amplifier (not depicted).

Figure 3B:
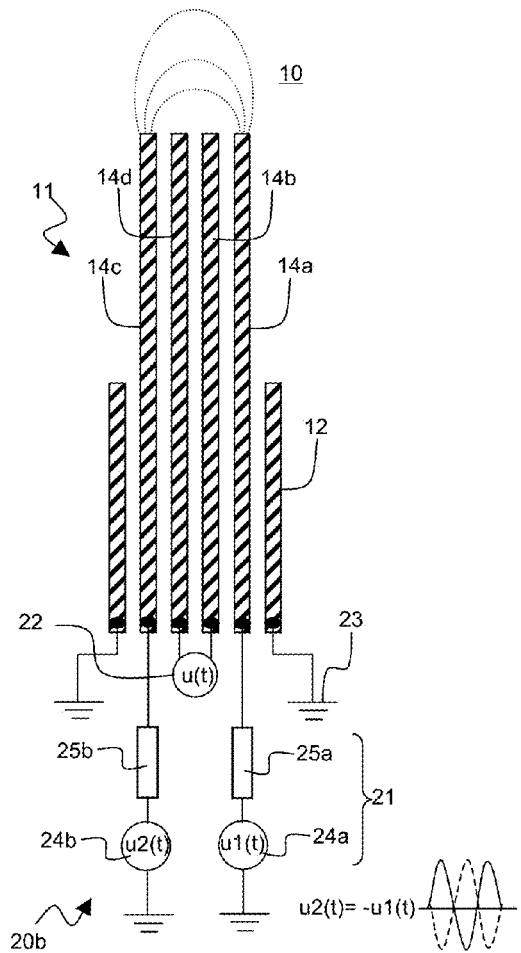

According to a second embodiment depicted on FIG. 3b, the measurement circuit 20b, adapted for a probe comprising four electrodes 14a, 14b, 14c, 14d, comprises two alternative voltage generators 24a, 24b. The alternative voltage generators 24a, 24b operates in phase opposition $u2(t)=-u1(t)$. The alternative voltage generators 24a, 24b are connected to the probe electrodes 14a, 14c through shunt resistors 25a, 25b, respectively, and form the excitation module 21. A voltage meter 22 forming a measuring module is connected to the detection electrodes 14b, 14d and measures the resulting voltage u(t). The detection electrodes 14b, 14d may be connected to an amplifier and a demodulation circuit (not shown). According to the second embodiment, the average voltage on probe electrodes 14b, 14d is therefore canceled both in time and space. Driving the excitation electrodes in phase opposition creates a dipole that cancels electric field at short distance from the probe tip.

Typical voltages u(t) measured are in the range of a few micro-volts to a few volts depending on probe designs, water conductivity and drive current from the measurement circuit.

Though the drawings shows the external tube 12 connected to the circuit ground 23, it may alternatively left floating from circuit ground in order to avoid current return through it.

The high frequency signal u(t) is then demodulated using a synchronous detection circuit or direct computation after digitalization (the demodulation is used to remove the high frequency parts of the signal).

Figure 4A:
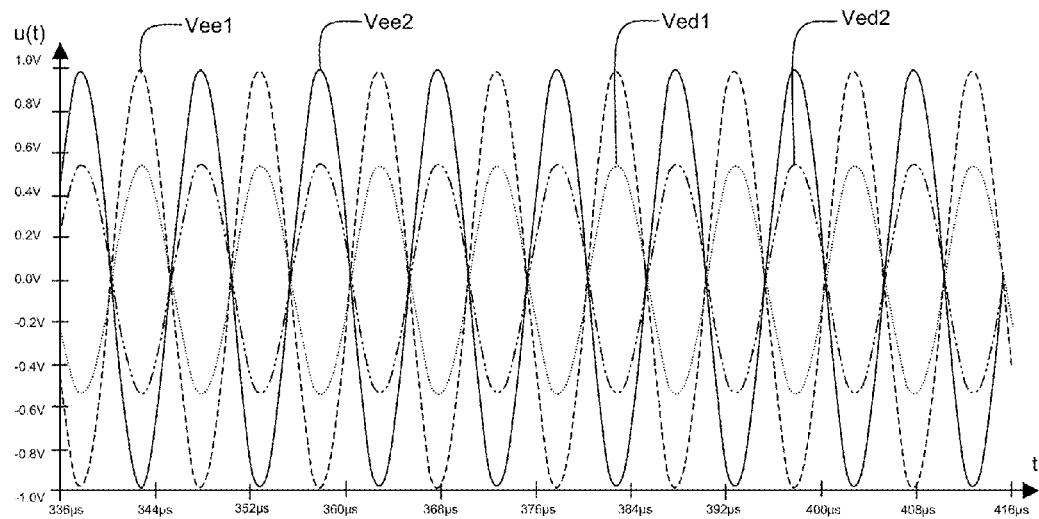
FIGS. 4a, 4b and 4c show examples of signals produced by means of the probe of FIG. 2.

FIG. 4a, shows signals u(t) observed with a four electrodes probe 14a, 14b, 14c, 14d, and the measurement circuit 20b according to the second embodiment (FIG. 3b).

In FIG. 4a, the signal Vee1 (short-dashed line) represents the voltage applied on the excitation electrode 14a, the excitation electrode being connected to the alternative voltage u1(t) generator 24a through the shunt resistor 25a. The signal Vee2 (continuous line) represents the voltage on the excitation electrode 14c, the excitation electrode being connected to the alternative voltage u2(t) generator 24b through the shunt resistor 25b. The alternative voltage u2(t) is the inverse of the alternative voltage u1(t) in order to cancel out electric field at distance from the tip. The signals Ved1 (dotted line) and Ved2 (alternately long- and double short-dashed line) represent the voltage on the detection electrodes 14b and 14d, respectively.

The embodiment of FIGS. 2a, 3c and 3d relates to a probe 11 comprising only two wire electrodes 14a, 14c instead of four as in the embodiment of FIG. 2b. The description relating to the structure of the probe of FIG. 2b is applicable otherwise. The electrical circuit in this case is different; there is no separate voltage detection circuit. As in the above-mentioned four wire embodiment, the measurement circuit may comprise two alternative voltage generators in phase opposition connected to the probe electrodes through shunt resistors. Both electrodes have the role of excitation electrode and detection electrode at the same time. The fluid resistivity is determined based on the measurement of the current flowing through the electrodes.

According to a third embodiment depicted on FIG. 3c, the measurement circuit 20c, adapted for a probe comprising two electrodes 14a, 14c, comprises an alternative current generator 21. The alternative current generator 21 operates at frequencies ranging from a few kilohertz to a few Mega Hertz, and drives a sinusoidal current i(t) ranging from a few µA to a few mA. The alternative current generator 21 is connected to the electrodes 14a, 14c. A voltage meter 22 is connected to the electrodes 14a, 14c and measures the resulting voltage u(t).

According to a fourth embodiment depicted on FIG. 3d, the measurement circuit 20d, adapted for a probe comprising two electrodes 14a, 14c, comprises two alternative voltage generators 24a, 24b. The alternative voltage generators 24a, 24b operates in phase opposition u2(t)=−u1(t). The alternative voltage generators 24a, 24b are connected to the electrodes 14a, 14c through shunt resistors 25a, 25b, respectively. A voltage meter 22 is connected to the electrodes 14a, 14c and measures the resulting voltage u(t).

Figure 4B:
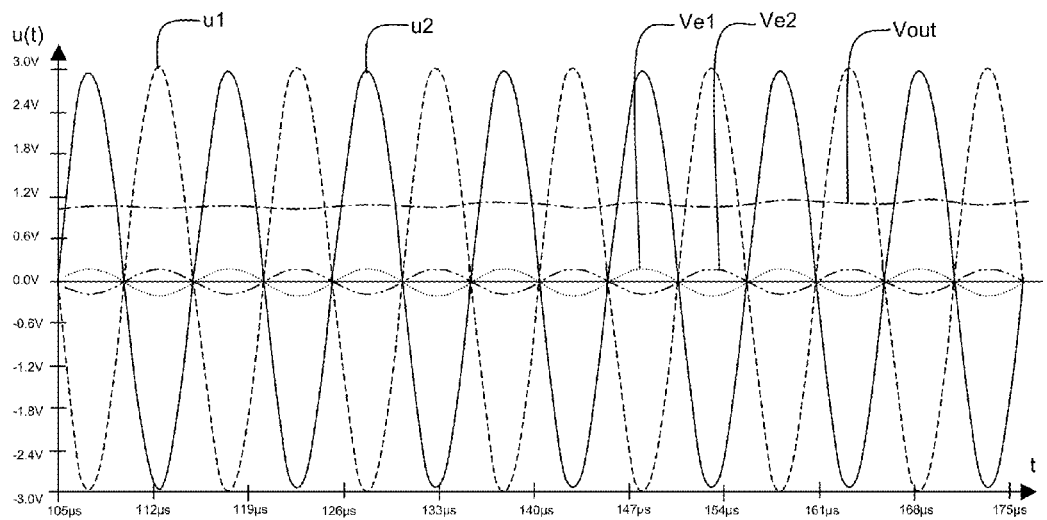

FIG. 4b shows signals u(t) observed with a two electrodes probe 14a, 14c, and the measurement circuit 20b according to the fourth embodiment.

The signal u1 (short-dashed line) represents the excitation voltage applied on the electrode 14a having the role of an excitation electrode, said electrode being connected to the alternative voltage u1(t) generator 24a. The signal u2 (continuous line) represents the voltage on the electrode 14b having the role of an excitation electrode, said electrode being connected to the alternative voltage u2( ) generator 24b. The signal Ve1 (dotted line) represents the voltage on electrode 14a having the role of a detection electrode. The signal Ve2 (alternately long- and double short-dashed line) represents the voltage on electrode 14b having the role of a detection electrode. The signal Vout (alternately long- and short-dashed line) represents the measurement circuit output after demodulation.

The principle of measurement is a local measurement of an electrical parameter of the fluid at the tip of the probe. The measured signal is related to conductivity at low frequency, and to resistivity at high frequency. Typically, water is a conductor while oil/gas is an insulator. Therefore, analyzing the measured signal enables discriminating a signal representative of water from a signal representative of oil/gas.

Figure 4C:
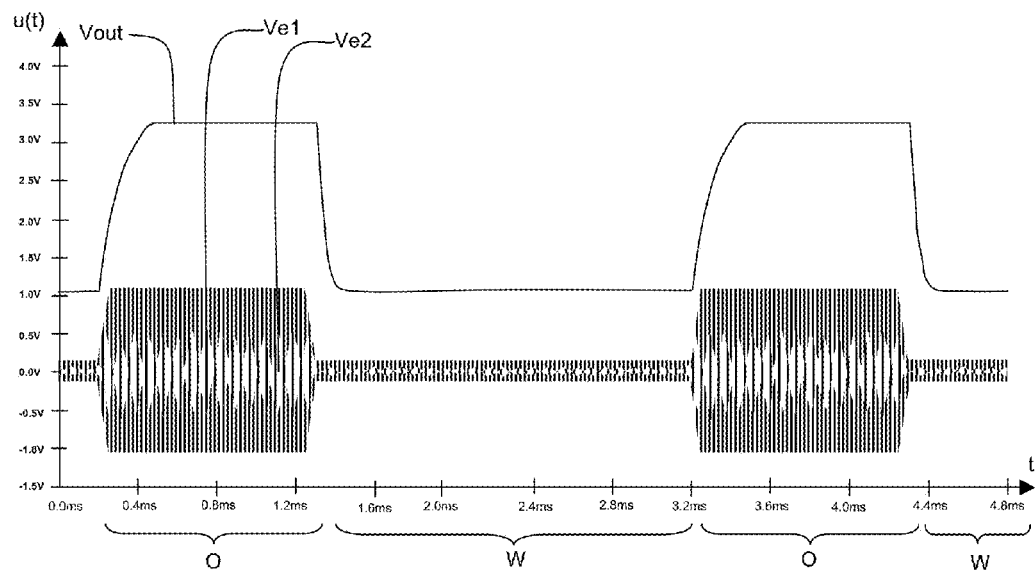

FIG. 4c shows the hereinbefore mentioned signals Ve1 and Ve2 on electrodes 14a and 14c and also the measurement circuit output Vout in multiphasic flow conditions. The measured output voltage Vout at a value around 1 V is interpreted as the flow of water W (small signal amplitude is characteristic of high conductive or low resistive fluid, namely water). The sudden increase in the measured output voltage Vout at a value around 1.2 V during a certain duration (plateau) is interpreted as the passage of a gas or oil O bubble (important signal amplitude is characteristic of low conductive or high resistive fluid, namely oil or gas). Thus, the measured signals show transitions from water W to gas or oil O. Based on such locally measured signals, a micro-controller is able to calculate various parameters related to the fluid flowing in a conduit, namely the holdup (by calculating the duration of signals representative of water vs the duration of signals representative of gas/oil during a defined time interval), the bubble count (by counting the number of plateaus during a defined time interval).

Figure 5:
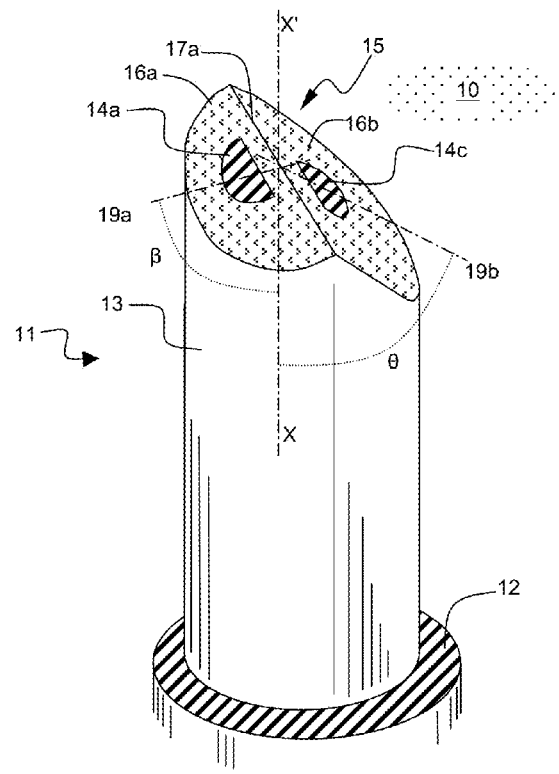
FIG. 5 shows modified geometries for the tip of the probe, the tip having inclined surfaces.

FIG. 5 shows another embodiment of a tip 15 having dissymmetrical geometries. The tip 15 is made up of planar surfaces 16a, 16b defining the tip end as a tip end line 17a, said surfaces being formed at different angles β, θ with respect to the central axis XX' of the probe 11. For example, the angle β is 30°, the angle θ is 45°. The electrodes 14a, 14c ends exposed to the fluid 10 emerge from the body 13 in the planar surfaces 16a, 16b, laterally from the tip end line 17a.

Figure 7A:
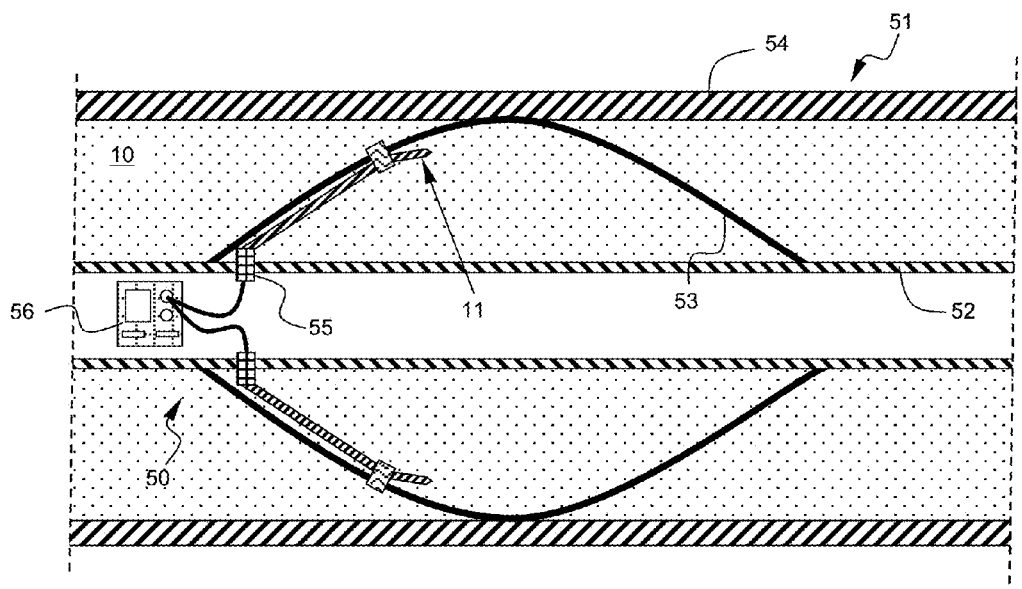
FIGS. 7a, 7b and 7c schematically show a measurement sonde including probes according to one of the above-mentioned embodiments.
Figure 7B:
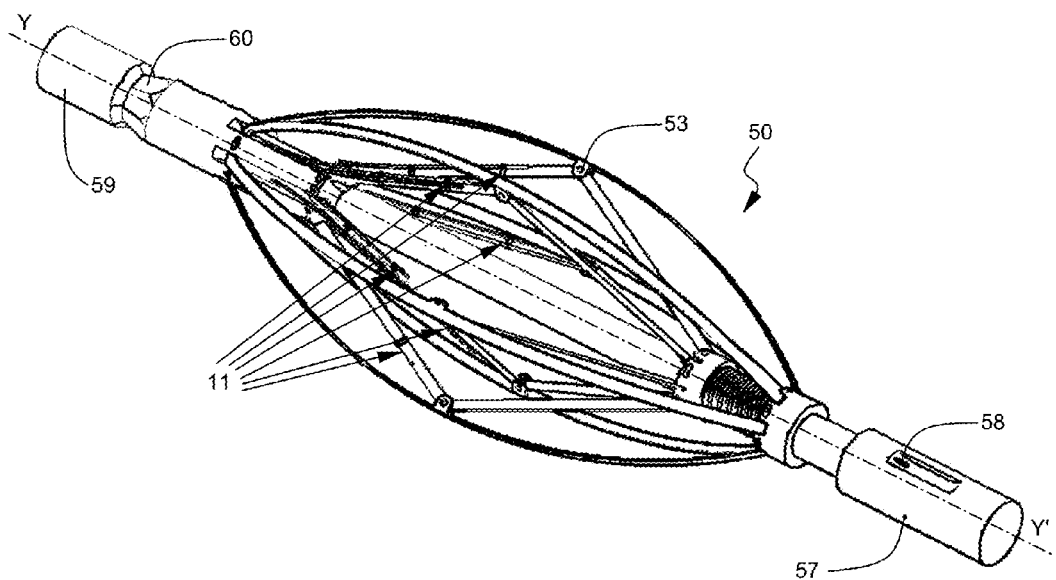
Figure 7C:
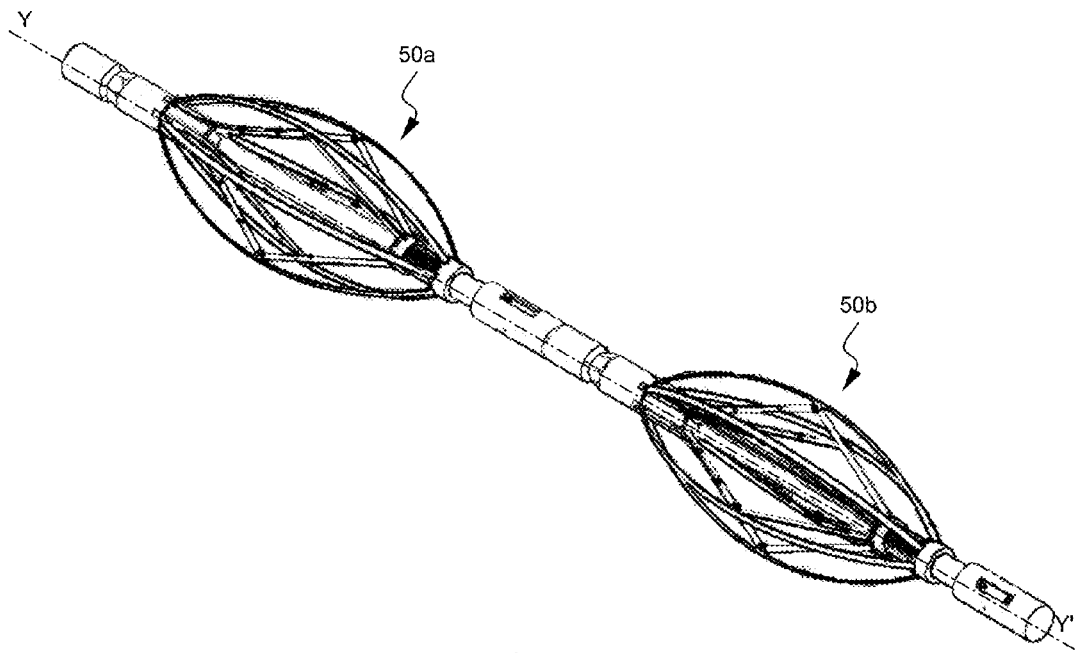

FIGS. 7a, 7b and 7c are schematic views of a measurement sonde 50 and a string of measurement sondes 50a, 50b adapted for operation in a hydrocarbon producing well 51, respectively. More precisely, FIG. 7a is a cross-section view schematically showing a probe 11 mounted in a measurement sonde 50 forming a wireline tool for production evaluation of hydrocarbon wells. FIG. 7b is a perspective view schematically showing a wireline tool for production evaluation of hydrocarbon wells which among other sensors such as pressure, temperature and flow sensors includes several probes 11. Each sonde 50, 50a, 50b has a central pressure-resistant rigid housing 52. The sonde 50, 50a, 50b carries external centralizers 53 adapted for contact with the production pipe walls 54 of the well 51. Multiple probes 11 as described above are secured on the inner face of the centralizers 53. The probes 11 may be located at angularly distributed locations with respect to the central axis YY' of the measurement sonde 50. Such a distributed probes arrangement solves the issue of measurement representativeness in inhomogeneous fluid flow as multiple measurements by multiple local probes become representative of the overall fluid flowing into the conduit of the well 51. Each probe 11 may be connected through a pressure feedthrough 55 to an electronic circuit 56 located inside the housing 52 of the sonde 50, 50a, 50b.

FIG. 7c is a perspective view schematically illustrating two measurement sondes 50a, 50b that are assembled in a string. Using at least two sondes allows cross correlation measurement on fluid holdups. Hydrocarbon wells production fluctuates with time, generating slugs and/or clouds of droplets or bubbles which propagate along the well. Measuring those corresponding variations using the probes of the invention installed in at least two measurement sondes allows deducing dispersed phase velocity and interpreting critical production parameter such as water, oil, gas entries in specific well sections.

The sonde depicted in FIGS. 7b and 7c may be connected endwise to other sonde sections carrying other types of fluid sensors such as pressure sensors 57, temperature sensors 58, flowrate sensors 59 and imager 60.

Figure 8:
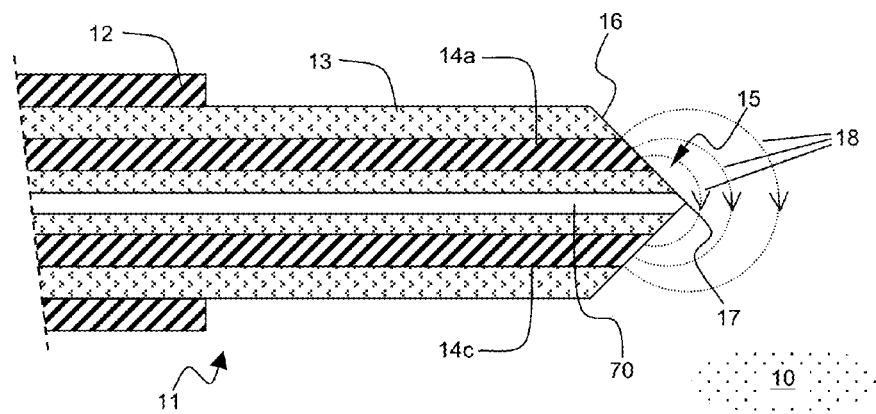
FIG. 8 shows a third embodiment of a probe according to the invention including an optical sensor.

FIG. 8 illustrates another embodiment wherein the multi-electrode probe 11 is integrated with an optical element 70. A sapphire rod 70 is suitably inserted in the central portion of the ceramic tube 13 and connected to an optical fiber (not shown). Light reflection at the tip 17 of the sapphire rod 70 relates to fluid 10 refractive index. Typical gas refractive index ranges from 1 to 1.2 depending on composition, temperature and pressure, distinct from liquids whose refractive index is ranging from 1.3 to 1.5. Therefore, the optical element can be used for refractive index and/or optical spectroscopic measurements. A key advantage of such design is to be able to detect the gas phase at the same time as water on a single probe thus achieving true three phase oil-water-gas detection on a single probe. Oil phase detection is deduced from the cases where neither water, nor gas is detected.

Figure 9:
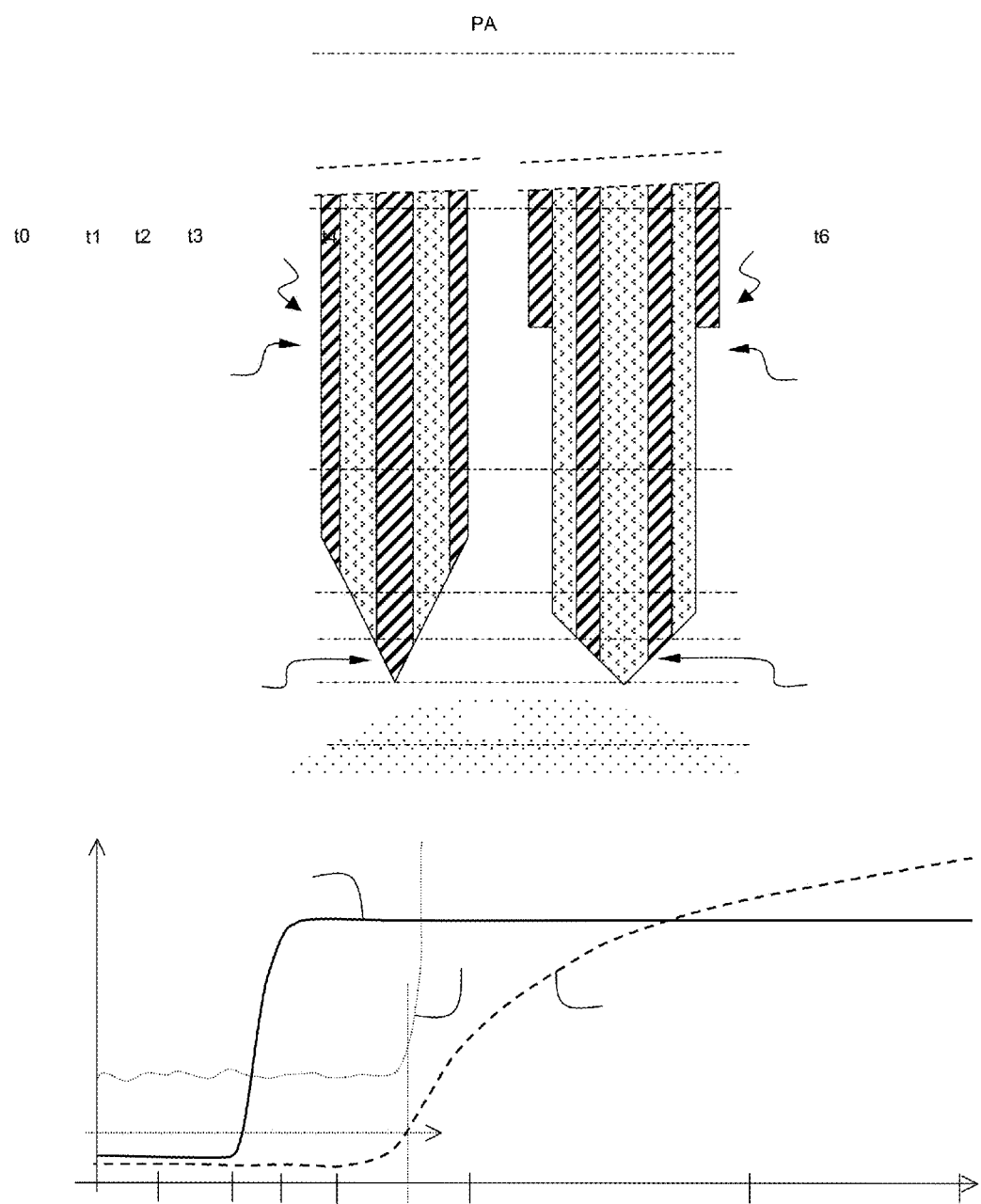
FIG. 9 show a probe according to the invention (top right) and according to the prior art (top left) and illustrates the propagation of oil/water front and typical probe response for said probes (bottom)

FIG. 9 illustrates the propagation of oil/water front (alternately long- and short-dashed line) and typical probe response u(t) (bottom) for a probe according to the prior art (top left) compared to a probe according to the invention (top right). The propagation of oil/water front relatively to the tip 5 and 15, respectively, of the probe 1 and 11, respectively, is illustrated for different time t1, t2, t3, t4, t5 and t6. The time t0 corresponds to an oil/water front before penetration. The time t0 corresponds to an oil/water front at the end of the tip. The time t1 corresponds to an oil/water front at the end of the tip. The times t2 to t4 correspond to an oil/water front positioned between the end of the tip and half penetration of the tip. The times t5 and t6 corresponds to an oil/water front at full penetration of the tip. The signal PA (dashed line) corresponds to the signal measured with the probe 1 according to the prior art. The signal INV (continuous line) corresponds to the signal measured with the probe 11 according to the invention.

With respect to the prior art probe 1, the maximum signal is reached when the water phase fully covers the probe ground offering a maximum surface for the current return (i.e. t being above t3, preferably around or superior to t4). This induces slow response and unstable levels as it depends on fluid and flow conditions (distribution of fluid far away from probe). This results in inaccurate measurement of water conductivity in multiphasic environments. In order to improve transition time from hydrocarbon to water, the prior art probe signal is amplified leading to saturation in conductive fluids and digital-like signals. As a consequence, the interpretation of water properties is impossible, at least difficult. Moreover, the phase holdups interpretation is highly sensitive to the selection of detection threshold. In practice this is a delicate matter as probe offset levels depends on capacitive couplings and electronics biases influenced by many uncontrolled parameters such as temperature, probe material ageing, humidity in tool chamber, electronics drift, etc. . . . An inappropriate threshold setting will lead to wrong phase interpretation. The signal AS (dotted line) corresponds to an amplified signal, the threshold tTAS being between t3 and t4.

In contradistinction, the probe 11 according to the invention provides a satisfactory measurement signal as soon as the end of the tip penetrates the oil/water front between times t1 and t2. Thus, the probe 11 according to the invention exhibits fast and stable response in such conditions allowing accurate fluid identification together with measurement of water conductivity even in dispersed multiphasic conditions.

The drawings and their description hereinbefore illustrate rather than limit the invention.

It should be appreciated that embodiments of the present invention are not limited to hydrocarbon wells (offshore and onshore) because the measuring method/probe/sonde of the present disclosure may be applied in various industries, for example the chemical industry, the aerospace industry, etc . . . where multiphase fluid properties are investigated. Furthermore, although some embodiments have drawings showing a horizontal well bore, said embodiments may also apply to a vertical or deviated well bore. In the frame of oilfield industry, all the embodiments of the present invention are equally applicable to cased and uncased borehole (open hole), and also other kind of conduits or device (e.g. a pump) where a fluid may flow. In other kind of industry, all the embodiments of the present invention may be implemented directly in the fluid medium (i.e. without the limitation of a conduit).

The invention claimed is:

1. A probe for producing signals indicative of a local phase composition of a fluid flowing in a well, comprising a body of electrically insulating material having a tip adapted for contact with the fluid flowing in the well, at least two electrodes of conductive material located in said body on opposite sides relatively to a central axis of the body and insulated from each other, said electrodes having ends exposed to the fluid flowing in the well located on either side of said tip, wherein said at least two electrodes, being simultaneously excitation and detection electrodes, said electrodes being adapted for connection to a measurement circuit comprising an excitation module in parallel with a measuring module, a signal in the electrodes measured by the measuring module being related to an electrical parameter indicative of the local phase composition of the fluid flowing in the well contacting the tip.

2. The probe according to claim 1, wherein the excitation module comprising a first alternative voltage generator connected to a first electrode through a first shunt resistor, and a second alternative voltage generator connected to a second electrode through a second shunt resistor, said first and second alternative voltage generators generating excitation signals in phase opposition.

3. The probe according to claim 1, further comprising an electronic board connected to the body and integrating the measurement circuit and a processing module so as to deliver digital measurements on an output cable.

4. The probe according to claim 1, further comprising a metal tube surrounding said body and acting as a shield.

5. The probe according to claim 1, wherein each electrode has a sheath of insulating material.

6. The probe according to claim 1, wherein the tip of the body is conical such as to define a tip conical surface, the electrodes ends exposed to the fluid flowing in the well emerging from the body in the tip conical surface, laterally from a tip end point.

7. The probe according to claim 1, wherein the tip of the body comprises two planar surfaces having different angles relatively to the central axis of the body, the electrodes ends exposed to the fluid flowing in the well emerging from the body in the planar surfaces, laterally from a tip end line.

8. The probe according to claim 1, further comprising an optical element located in the central portion of the body, an end portion of said optical element forming the end of the probe tip.

9. A probe for producing signals indicative of a local phase composition of a fluid flowing in a well, comprising a body of electrically insulating material having a tip adapted for contact with the fluid flowing in the well, at least two electrodes of conductive material located in said body on opposite sides relatively to a central axis of the body and insulated from each other, said electrodes having ends exposed to the fluid flowing in the well located on either side of said tip, wherein a first pair of electrodes, being excitation electrodes, located in a first plane intersecting the central axis of the body, and a second pair of electrodes, being detection electrodes, located in a second plane intersecting the central axis of the body and at angle with the first plane, said first pair of electrodes being adapted for connection to an excitation module, said second pair of electrodes being adapted for connection to a measuring module.

10. The probe according to claim 9, further comprising an electronic board connected to the body and integrating the measurement circuit and a processing module so as to deliver digital measurements on an output cable.

11. The probe according to claim 9, wherein the excitation module comprising a first alternative voltage generator connected to a first electrode through a first shunt resistor, and a second alternative voltage generator connected to a second electrode through a second shunt resistor, said first and second alternative voltage generators generating excitation signals in phase opposition.

12. The probe according to claim 9, further comprising a metal tube surrounding said body and acting as a shield.

13. The probe according to claim 9, wherein each electrode has a sheath of insulating material.

14. The probe according to claim 9, wherein the tip of the body is conical such as to define a tip conical surface, the electrodes ends exposed to the fluid flowing in the well emerging from the body in the tip conical surface, laterally from a tip end point.

15. The probe according to claim 9, wherein the tip of the body comprises two planar surfaces having different angles relatively to the central axis of the body, the electrodes ends exposed to the fluid flowing in the well emerging from the body in the planar surfaces, laterally from a tip end line.

16. The probe according to claim 9, further comprising an optical element located in the central portion of the body, an end portion of said optical element forming the end of the probe tip.

17. A measurement sonde adapted for displacement along and within a well, comprising a plurality of probes for producing signals indicative of a local phase composition of a fluid flowing in the well, each probe comprising a body of electrically insulating material having a tip adapted for contact with the fluid flowing in the well, at least two electrodes of conductive material located in said body on opposite sides relatively to a central axis of the body and insulated from each other, said electrodes having ends exposed to the fluid flowing in the well located on either side of said tip, wherein the plurality of probes are located at angularly distributed locations with respect to a central axis of the measurement sonde, wherein each probe comprises two electrodes, being simultaneously excitation and detection electrodes, said electrodes being adapted for connection to a measurement circuit comprising an excitation module in parallel with a measuring module, a signal in the electrodes measured by the measuring module being related to an electrical parameter indicative of the local phase composition of the fluid flowing in the well contacting the tip.

18. The measurement sonde according to claim 17, wherein the excitation module comprises a first alternative voltage generator connected to a first electrode through a first shunt resistor, and a second alternative voltage generator connected to a second electrode through a second shunt resistor, said first and second alternative voltage generators generating excitation signals in phase opposition.

19. The measurement sonde according to claim 17, wherein each probe further comprises an electronic board connected to the body and integrating the measurement circuit and a processing module so as to deliver digital measurements on an output cable, the output cable being connected to an electronic circuit located inside an housing of the measurement sonde by means of a pressure feedthrough.

20. The measurement sonde according to claim 17, wherein each probe further comprises a metal tube surrounding the body and acting as a shield.

21. The measurement sonde according to claim 17, wherein each electrode has a sheath of insulating material.

22. The measurement sonde according to claim 17, wherein each probe further comprises a metal tube surrounding the body and acting as a shield.

23. The measurement sonde according to claim 17, wherein each electrode has a sheath of insulating material.

24. The measurement sonde according to claim 17, wherein the tip of the body is conical such as to define a tip conical surface, the electrodes ends exposed to the fluid flowing in the well emerging from the body in the tip conical surface, laterally from a tip end point.

25. The measurement sonde according to claim 17, wherein the tip of the body comprises two planar surfaces having different angles relatively to the central axis of the body, the electrodes ends exposed to the fluid flowing in the well emerging from the body in the planar surfaces, laterally from a tip end line.

26. The measurement sonde according to claim 17, wherein at least one probe further comprises an optical element located in the central portion of the body, an end portion of said optical element forming the end of the probe tip.

27. The measurement sonde according to claim 17, wherein the well is a hydrocarbon well, and wherein the measurement sonde carries centralizers, the plurality of probes being secured to the centralizers.

28. Measurement sonde adapted for displacement along and within a well, comprising a plurality of probes for producing signals indicative of a local phase composition of a fluid flowing in the well, each probe comprising a body of electrically insulating material having a tip adapted for contact with the fluid flowing in the well, at least two electrodes of conductive material located in said body on opposite sides relatively to a central axis of the body and insulated from each other, said electrodes having ends exposed to the fluid flowing in the well located on either side of said tip, wherein the plurality of probes are located at angularly distributed locations with respect to a central axis of the measurement sonde, wherein each probe comprises a first pair of electrodes, being excitation electrodes, located in a first plane intersecting the central axis of the body, and a second pair of electrodes, being detection electrodes, located in a second plane intersecting the central axis of the body and at angle with the first plane, said first pair of electrodes being adapted for connection to an excitation module, said second pair of electrodes being adapted for connection to a measuring module.

29. The measurement sonde according to claim 28, wherein the excitation module comprises a first alternative voltage generator connected to a first electrode through a first shunt resistor, and a second alternative voltage generator connected to a second electrode through a second shunt resistor, said first and second alternative voltage generators generating excitation signals in phase opposition.

30. The measurement sonde according to claim 28, wherein each probe further comprises an electronic board connected to the body and integrating the measurement circuit and a processing module so as to deliver digital measurements on an output cable, the output cable being connected to an electronic circuit located inside an housing of the measurement sonde by means of a pressure feedthrough.

31. The measurement sonde according to claim 28, wherein the tip of the body is conical such as to define a tip conical surface, the electrodes ends exposed to the fluid flowing in the well emerging from the body in the tip conical surface, laterally from a tip end point.

32. Measurement sonde according to claim 28, wherein the tip of the body comprises two planar surfaces having different angles relatively to the central axis of the body, the electrodes ends exposed to the fluid flowing in the well emerging from the body in the planar surfaces, laterally from a tip end line.

33. The measurement sonde according to claim 28, wherein at least one probe further comprises an optical element located in the central portion of the body, an end portion of said optical element forming the end of the probe tip.

34. The measurement sonde according to claim 28, wherein the well is a hydrocarbon well, and wherein the measurement sonde carries centralizers, the plurality of probes being secured to the centralizers.

35. A method for producing signals indicative of a local phase composition of a fluid flowing in a well, comprising the steps of:
inserting at least one probe in the well, said probe comprising a body of electrically insulating material having a tip adapted for contact with the fluid flowing in the well, at least two electrodes of conductive material located in said body on opposite sides relatively to a central axis of the body and insulated from each other, said electrodes having ends exposed to the fluid located on either side of said tip,
applying an excitation signal on two electrodes, said electrodes being excitation electrodes,
measuring a detection signal related to an electrical parameter indicative of the local phase composition of the fluid flowing in the well contacting the tip on two electrodes, said electrodes being detection electrodes.

* * * * *